United States Patent [19]

Berry et al.

[11] 4,197,009
[45] Apr. 8, 1980

[54] PHOTOACOUSTIC RAMAN SPECTROSCOPY

[75] Inventors: Michael J. Berry, Chatham; Joseph J. Barrett, Morris Plains, both of N.J.

[73] Assignee: Allied Chemical Corporation, Morris Township, Morris County, N.J.

[21] Appl. No.: 909,859

[22] Filed: May 26, 1978

[51] Int. Cl.² .............................................. G01J 3/44
[52] U.S. Cl. .................................................. 356/301
[58] Field of Search ................. 250/343, 344; 356/301

[56] References Cited

U.S. PATENT DOCUMENTS

| | | | |
|---|---|---|---|
| 3,973,134 | 8/1976 | Begley et al. ......................... 250/574 |
| 4,044,257 | 8/1977 | Kreuzer ............................. 250/343 X |
| 4,051,372 | 9/1977 | Aine ..................................... 250/343 |
| 4,068,125 | 1/1978 | Bell .................................. 250/343 X |
| 4,077,719 | 3/1978 | Barrett ................................. 356/301 |

Primary Examiner—F. L. Evans
Attorney, Agent, or Firm—Ernest D. Buff; Gerhard H. Fuchs

[57] ABSTRACT

A method and apparatus for spectroscopic material anaylsis are provided. Two coherent beams 15, 17 of monochromatic radiation are directed through a sample of material. A tuning mechanism 14 adjusts the frequency difference between the radiation beams 15, 17 to equal substantially the vibrational frequency of a preselected constituent of the material. Molecular energy of a preselected constituent of the material is increased, thereby producing a detectable signal 22 in the form of a pressure wave. The signal is received by a detecting mechanism 24 which indicates the magnitude thereof.

7 Claims, 6 Drawing Figures

PHOTOACOUSTIC RAMAN SPECTROSCOPY

BACKGROUND OF THE INVENTION

This invention relates to the field of spectroscopy and more particularly to a method and apparatus in which two coherent beams of monochromatic light are transmitted through a sample of material at a frequency differential correlated with the vibrational frequency of a constituent to detect and quantitatively measure the constituent.

DESCRIPTION OF THE PRIOR ART

In the apparatus used for spectroscopic material analysis, a modulated beam of infrared radiation having an emission spectrum embracing the absorption spectrum of the gas to be analyzed is directed through an optoacoustic cell containing the gas. Energy absorbed from the beam by the gaseous material heats the gas, thereby producing an acoustic wave. The latter is detected by a microphone in contact with the gas and converted to an electrical signal that is a function of the infrared radiation wavelength to provide an absorption spectrum of the gas.

One of the major problems with such apparatus is its unsuitability for universal analysis of minute quantities of gaseous constituents. The frequency of high power infrared radiation required for acceptable detection sensitivity is varied over a narrow range that does not embrace the absorption spectra of many gases. Another problem with such apparatus is the difficulty of fine tuning the infrared radiation beam. The infrared radiation frequency cannot be easily tuned to match absorption line frequency of the gas being analyzed, with the result that the absorption efficiency, and hence the detection sensitivity of the apparatus, is reduced. To alleviate such problems, it has been necessary to provide the apparatus with highly sensitive forms and combination of detectors, filters, control systems and the like, which are relatively expensive.

SUMMARY OF THE INVENTION

The present invention provides apparatus having increased sensitivity for spectroscopic material analysis. The apparatus has radiation source means for generating two coherent beams of monochromatic radiation. Such radiation source means has a tuning means associated therewith for adjusting the frequency difference between said beams of radiation to equal substantially the vibrational frequency of a preselected constituent of the material. A projecting means is provided for directing the beams of radiation through the material to increase molecular energy of a preselected constituent thereof and thereby produce a detectable signal in the form of a pressure wave. The signal is received by a detecting means, which indicates the magnitude thereof.

Further, the invention provides a method for spectroscopically analyzing material comprising the steps of generating two coherent beams of monochromatic radiation; adjusting the frequency difference between the beams of radiation to equal substantially the vibrational frequency of a preselected constituent of the material; directing the beams of radiation through the material to produce a detectable signal in the form of a pressure wave; and indicating the magnitude of the signal.

BRIEF DESCRIPTION OF THE DRAWINGS

The invention will be more fully understood and further advantages will become apparent when reference is made to the following detailed description of the preferred embodiments of the invention and the accompanying drawings in which:

FIG. 6 is a chart showing photoacoustic signals generated in carbon dioxide gas using pulsed radiation.

DESCRIPTION OF THE PREFERRED EMBODIMENTS

Radiation capable of exciting vibrational states is found in each of the visible, infrared and ultraviolet frequency regions. As a consequence, the invention will function with radiation having a relatively wide range of frequencies. For illustrative purposes, the invention is described in connection with method and apparatus for exciting vibrational spectra of gaseous material with radiation from the visible frequency region. When applied in this manner, the invention is particularly suited to detect and to measure quantitatively minor constituents of a gaseous material such as air. It will be readily appreciated that the invention can be practiced using radiation from any of the foregoing frequency regions, and that it can be employed for similar and yet diversified uses, such as the analysis of vibrational spectra of liquids and solids, the determination of molecular gas constants and the like.

Figure 1:
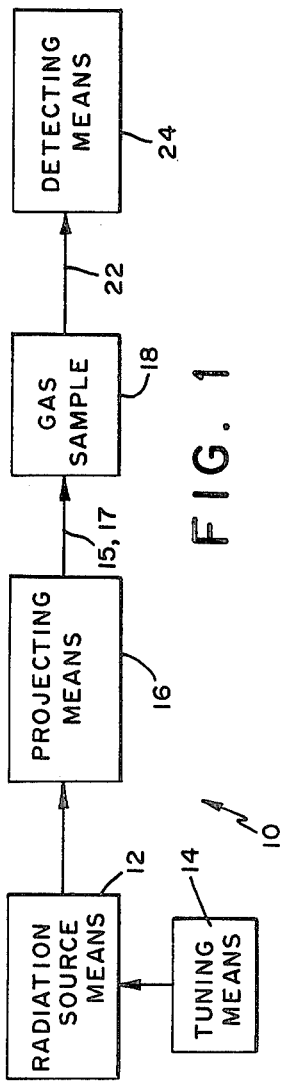
FIG. 1 is a block diagram showing apparatus for spectroscopic material analysis.

Referring to FIG. 1 of the drawings, there is shown preferred apparatus for spectroscopic gas analysis. The apparatus, shown generally at 10, has radiation source means 12 for generating two coherent beams 15, 17 of monochromatic radiation. The radiation source means 12 has associated therewith a tuning means 14 for adjusting the frequency difference between the beams of radiation to equal substantially the vibrational frequency of a preselected constituent of material. A projecting means 16 is provided for directing the beams of radiation 15, 17 through gaseous material in compartment 18 to increase molecular internal energy (e.g. vibrational and rotational energy) of a preselected species of the gaseous material. Due to molecular collisions of the preselected species with like species or different constituents of the gaseous material, molecular energy transfer occurs, thereby producing a detectable signal 22 in the form of a pressure wave. The molecular energy transfer is typically in the form of a vibrational to translational transfer, but may be in the form of rotational to translational transfer, electronic to translation energy transfer, a hybrid of vibrational and rotational to translational energy transfer and the like. A detecting means 24, adapted to measure the pressure wave, indicates the magnitude thereof.

Figure 2:
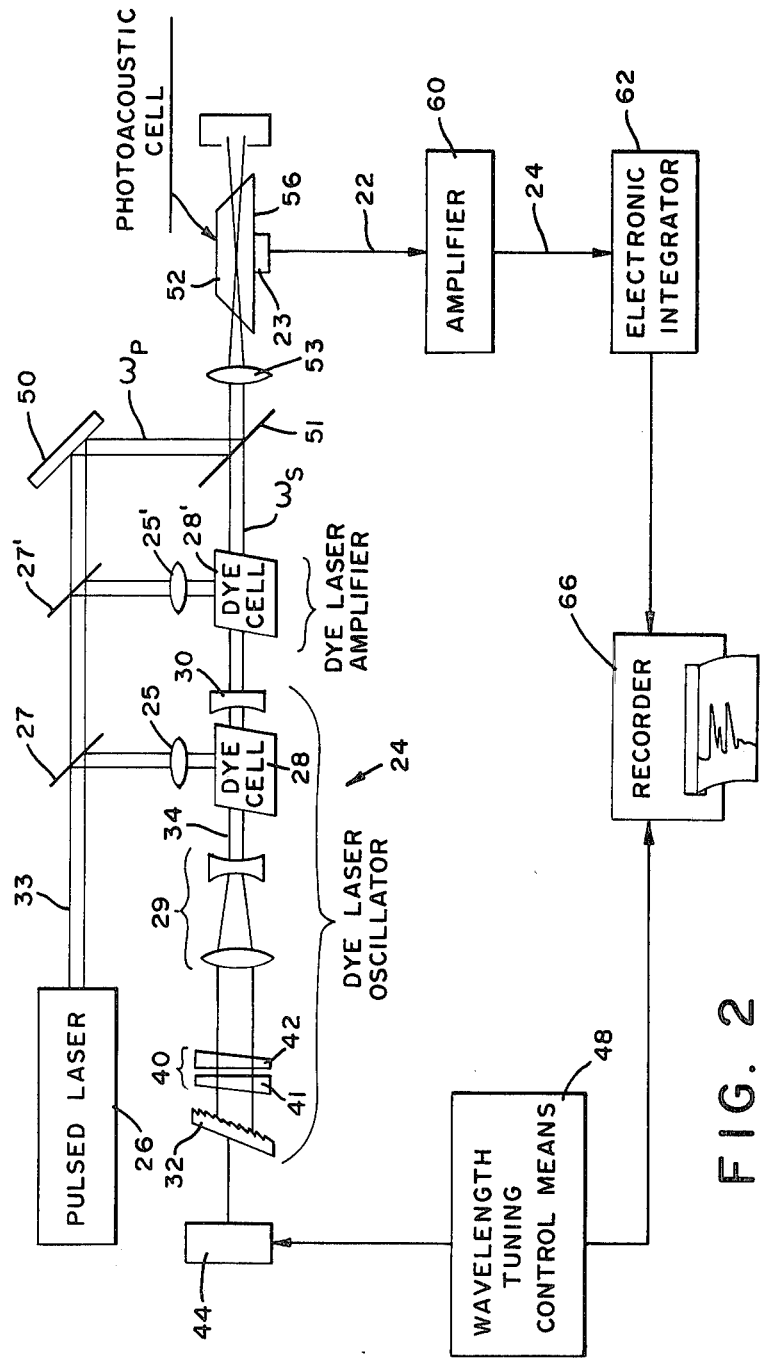
FIG. 2 is a schematic diagram of the apparatus of FIG. 1.

More specifically, as shown in FIG. 2, the radiation source means 12 can comprise a dye laser shown generally at 24 adapted to be excited by energy from pulsed laser 26, which may be a pulsed nitrogen laser, a frequency doubled pulsed Nd:YAG laser or the like. Such dye laser 24 includes (1) a cell 28 containing dye material and (2) a laser cavity comprised of a partially transmitting output mirror 30 and an optical element 32. In addition, the dye laser 24 can include a lens 25 and mirror 27 for directing pulsed radiation 33 into cell 28. A dye laser amplifier including dye cell 28', lens 2' and mirror 27' receives and amplifies radiation from output mirror 30. The dye materials which are suitable for use in the dye laser 24 are any of those conventionally employed which, when excited, emit light having frequencies in the transparency range of the gaseous material being analyzed. Typical dye materials include Rhodamine 6G, Kiton Red, Cresyl Violet, Nile Blue and the like.

Radiation emitted from the dye material in dye cell 28 is continuously tunable over a wide frequency range. A tuning means 14 associated with the dye cavity 24 adjusts the frequency of beam 34 relative to the frequency of beam 33 to provide a frequency difference between beams 34 and 33 that is equal to a vibrational frequency of a preselected constituent of the gaseous material. Beam 34 is transmitted from the radiation source means 12 via output mirror 30. Generation of the detectable signal 22 is most efficient when the radiation emitted from the dye laser 24 has a line width and frequency stability about equal to or less than the line width of the vibrational spectra of the material appointed for detection.

The tuning means 14 can include a varying number of optical components assembled in a variety of combinations. In one embodiment of the apparatus 10, the tuning means 14 comprises a diffraction grating 32 mounted in autocollimation in combination with a beam expanding telescope 29. Telescope 29 is disposed in series with and between dye cell 28 and diffraction grating 32 for enlarging the width of the dye laser beam 34 and thereby improving the efficiency of the diffraction grating 32. The tuning means 14 can additionally comprise a Fabry-Perot interferometer 40 disposed in series with and between the beam expanding telescope 29 and the diffraction grating 32 for further restricting the frequency bandwidth of the dye laser beam 34. Fine frequency tuning of the Fabry-Perot interferometer 40 may be accomplished by changing the pressure of the gas between the Fabry-Perot mirrors 41 and 42. Alternatively, the Fabry-Perot interferometer 40 could consist of a solid Fabry-Perot etalon. For this embodiment, fine frequency tuning could be achieved by rotating the etalon about an axis perpendicular to the direction of the dye laser beam 34. The diffraction grating 32 is connected through a shaft encoded stepping motor 44 to a wavelength timing control means 48 adapted to vary the rotational velocity of stepping motor 44 relative to the fine frequency tuning of the Fabry-Perot interferometer 40 so as to produce synchronous scanning of the diffraction grating 32 and the Fabry-Perot interferometer 40. An electrical signal from the wavelength tuning control means 48 is directed into a recording means 66 for indicating the wavelength of the dye laser 24. The frequency of the dye laser beam 34 is tuned so that the frequency difference between the pulsed laser beam 33 and the dye laser beam 34 equals substantially the vibrational frequency of a preselected constituent of gaseous material.

A projecting means 16 comprising mirror 50, beam combiner 51 and focusing lens 53 is used to introduce the two coherent beams of monochromatic radiation 15, 17 into gaseous material in sample compartment 52 in one direction, which will be considered to be substantially horizontal for convenience in referencing directions but may, of course, be in any direction desired. A pressure wave resulting from increased molecular energy of a preselected species of the gaseous material in sample compartment 52 is detected by acoustical detecting means 23 disposed in wall 56 of compartment 52 so as to be in contact with the gaseous material therein.

Several known acoustical detecting means may be used with the apparatus 10. Preferably, the acoustical detecting means 23 is a microphone adapted to contact the gaseous material in sample 52 and transmit an electrical signal, the magnitude of which varies in proportion to pressure changes produced in the gaseous material by the radiation beams 15, 17. The signal 22 from microphone 23, typically in the audio frequency range, is amplified by amplifier 60 and transmitted to an integrator 62 which accumulates and adds the amplified signal 24 over some predetermined time interval. The output of integrator 62 is applied to recorder 66, which indicates the magnitude thereof.

Before describing how the apparatus of FIG. 2 can be used to determine the magnitude of signal 22, it would be helpful to explain the principles underlying photoacoustic Raman spectroscopy. It is possible to observe photoacoustic Raman scattering in different media (solid, liquid and gaseous samples). Thus, even though the following description is directed to photoacoustic Raman scattering in gas, it will be understood that the principles of the photoacoustic Raman technique set forth below apply to solid and liquid media as well.

If a gaseous sample is illuminated by two laser beams, which are temporally and spatially coincident, interactions can occur which produce selective population of a given energy level of the sample. The conditions for which this selective population occurs are: (1) the transition involving the given energy level must be Raman-active, i.e., the transition must involve a change in the molecular polarizability, and (2) the frequency difference of the two incident laser beams must be adjusted to equal the frequency of this Raman-active transition. Raman-active transitions can occur for molecules that have no infrared spectrum, since the occurrence of a Raman spectrum depends on the change in polarizability of the molecule and not on the presence of a permanent dipole moment. The selective population of a given energy level is accomplished by the mechanism of coherent Raman amplification, which is the nonlinear optical process associated with stimulated Raman scattering. As the excited molecules in this energy level relax through collisions, a pressure wave is generated which is detected by a sensitive microphone.

Figure 3:
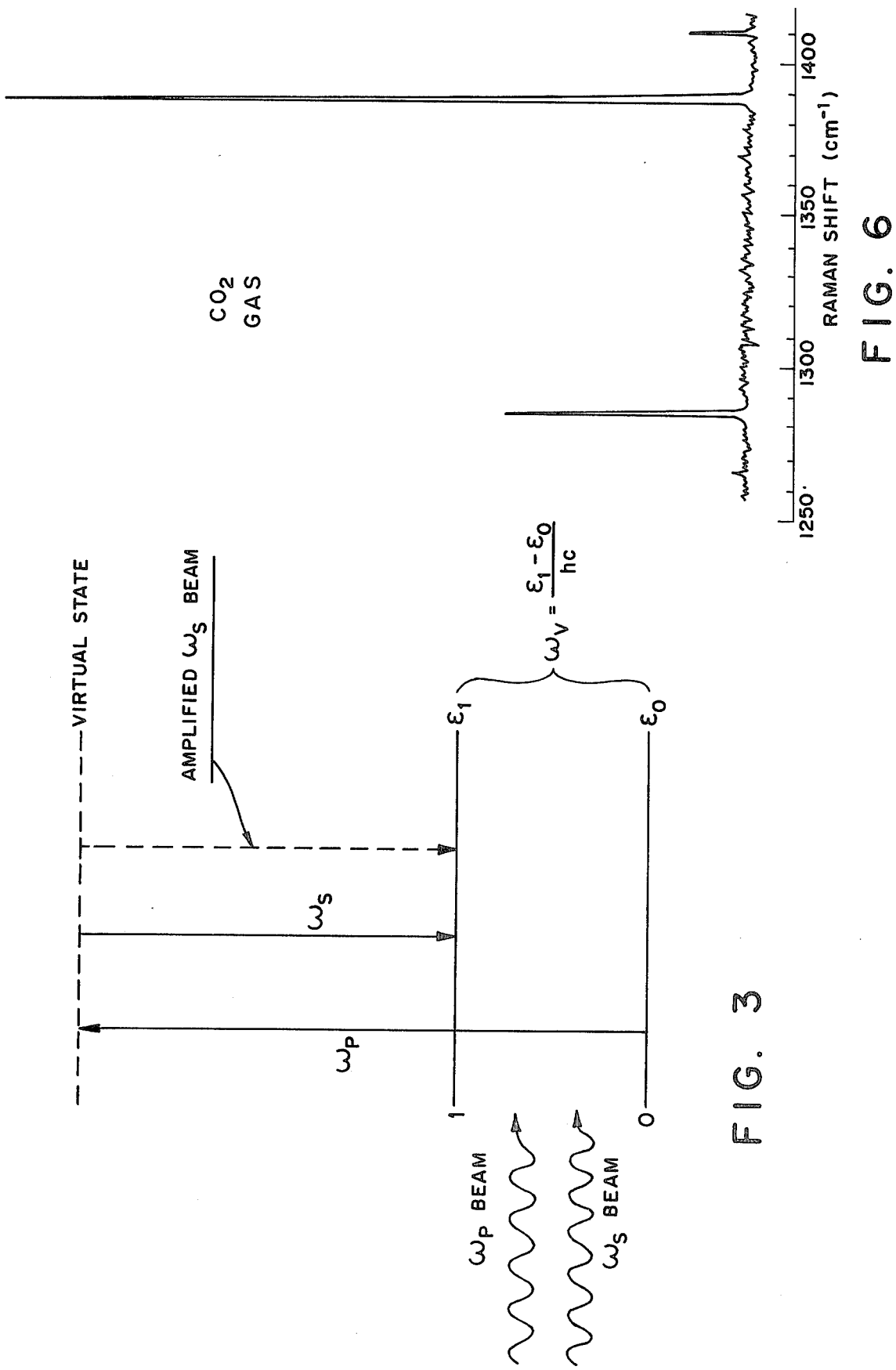
FIG. 3 is a schematic representation depicting the relationship between the energy levels of a gaseous constituent and the input laser frequencies $\omega_p$ and $\omega_s$.

A schematic representation of the photoacoustic Raman scattering process is shown in FIG. 3. Two incident laser beams with wavenumber frequency $\omega_p$ and $\omega_s$ interact with two energy states (labelled 0 and 1) of a molecule. The laser beam at the frequency $\omega_p$ is referred to as the pump beam and the second laser beam at the frequency $\omega_s$ is referred to as the Stokes beam. If $E_0$ and $E_1$ are the energies (in units of ergs) associated with the levels 0 and 1, then the wavenumber frequency for the Raman transition between those energy states is equal to $(E_1 - E_0)/hc$, where h is Planck's constant $(6.626 \times 10^{-27}$ erg·sec) and c is the speed of light ($\sim 3 \times 10^{10}$ cm/sec). If levels 0 and 1 are vibrational energy levels of the molecule, then $(E_1-E_0)/hc=\omega_v$ is a vibrational Raman frequency. When the frequencies of the incident lasers are adjusted such that $\omega_p-\omega_s=\omega_v$, the nonlinear interaction between the $\omega_p$ and $\omega_s$ beams, by means of the third-order nonlinear susceptibility $\chi^{(3)}(\omega_s)$, produces an amplification of the Stokes beam and an attenuation of the pump beam. For each Stokes photon which is generated by this interaction, one molecule is transferred from level 0 to level 1. An excess population in level 1 is produced and the translational energy of the molecules in the gas sample is increased by collisional deactivation of the excess population in level 1. This increase in the molecular translational energy produces a pressure change which is detected by a microphone in (or attached to) the gas sample cell.

$E_p$, $I_p$ and $E_s$, $I_s$ represent the electric field and intensity (power/unit area) for the collinear pump and Stokes beam, respectively, which are propagating in the positive Z direction through the gas sample. The temporal and spatial variations of the electric field for the Stokes beam only (in the absence of the pump beam) is $$E_s = \tilde{E}_s \exp\{i(\omega_s t - k_s Z)\} \tag{1}$$

where $E_s$ is the electric field amplitude and $k_s$ is the magnitude of the Stokes wavevector. When the pump beam is present simultaneously with the Stokes beam, a nonlinear interaction occurs which modifies the Stokes wavevector by the addition of a second term as shown below $$k'_s = k_s[1 + \frac{\chi^{(3)}(\omega_s)}{2\mu_s^2}|\tilde{E}_p|^2] \tag{2}$$

$$= k_s[1 + \frac{|\tilde{E}_p|^2}{2\mu_s^2}(\chi' - i\chi'')]$$

where $\mu_s$ is the refractive index at $\omega_s$ and $\chi^{(3)}(\omega_s)$ is the third-order nonlinear susceptibility at the Stokes frequency $\omega_s$. The susceptibility $\chi^{(3)}(\omega_s)$ is a complex quantity which is the sum of a resonant part and a nonresonant part. The explicit form of $\chi^{(3)}(\omega_s)$ is $$\chi^{(3)}(\omega_s) = (\chi' - i\chi'')_R + \chi_{NR} \tag{3}$$

$$= \frac{N\Delta_V}{8\pi^4 hc\omega_s^4}\left(\frac{d\sigma}{d\Omega}\right)\frac{\omega_V}{\omega_V^2 - (\omega_p - \omega_s)^2 + i\Gamma(\omega_p - \omega_s)}$$

$$+ \chi_{NR}$$

where the subscripts R and NR represent the resonant and nonresonant components, respectively. The nonresonant component, $\chi_{NR}$, is a real quantity which is due to the electronic contribution to the susceptibility. Usually, $\chi_{NR}$ is several orders of magnitude smaller than the resonant susceptibility for strong Raman transitions in pure materials. At resonance, the frequency difference between the pump and Stokes beams obeys the relation $\omega_p-\omega_s=\omega_V$ and the real part of $\chi^{(3)}$ is equal to $\chi_{NR}$ only since $\chi'=0$ and the imaginary part is equal to $$\chi'' = -\left(\frac{d\sigma}{d\Omega}\right)\frac{N\Delta_V}{8\pi^4 hc\omega_s^4 \Gamma} \tag{4}$$

where

N = the molecular number density
$\Delta_V$ = the fractional population difference between levels 0 and 1.
$[d\sigma/d\Omega]$ = the spontaneous Raman scattering cross-section
$\Gamma$ = the full width at half maximum Raman linewidth in units of cm$^{-1}$ and
$\omega_s$ = the frequency of the Stokes beam in units of cm$^{-1}$.

The electric field of the Stokes wave after having travelled a distance Z through the gas sample is $E_s'(Z)$ which is given by the equation $$E_s'(Z) = \tilde{E}_s \exp[i(\omega_s t - k_s' Z)]$$
$$= \tilde{E}_s'(Z)\exp[i(\omega_s t - k_s Z - k_s \frac{|\tilde{E}_p|^2}{2\mu_s^2}\chi' Z)] \tag{5}$$

where $$\tilde{E}_s'(Z) = \tilde{E}_s \exp[-k_s \frac{|\tilde{E}_p|^2}{2\mu_s^2}\chi'' Z]. \tag{6}$$

Since the relationship between the intensity (power per unit area) and the electric field amplitude of a light wave is given by the equation $I = c|\tilde{E}|^2/8\pi$, the term $$\exp[-ik_s \frac{|\tilde{E}_p|^2}{2\mu_s^2}\chi' Z].$$

gives rise to a spatial modulation of the refractive index of the gas sample, the magnitude of which depends on the intensity of the pump beam. The intensity of the amplified Stokes wave after traversing a distance Z through the gas sample is $$I_s(Z) = c/8\pi |\tilde{E}_s'|^2. \tag{7}$$

Using equation 6, equation 7 can be written in the form $$I_s(Z) = I_s(o)e^{g(\omega_s)Z} \tag{8}$$

where $I_s(o)$ is the initial intensity of the Stokes beam (at Z=0) and $g(\omega_s)$ is the gain coefficient (in units of 1/cm) at the Stokes frequency given by the equation $$g(\omega_s) = -k_s \frac{|\tilde{E}_p|^2}{\mu_s^2}\chi''. \tag{9}$$

Substituting for $k_s(=2\pi\mu_s\omega_s)$, $|\tilde{E}_p|^2$ and $\chi''$ yields $$g(\omega_s) = \frac{2N\Delta_V I_p}{hc^2\pi^2\mu_s\omega_s^3\Gamma}\left(\frac{d\sigma}{d\Omega}\right) \tag{10}$$

where $I_p$ is the pump intensity in units of ergs/sec/cm$^2$. The amplified Stokes intensity is $$\Delta I_s \equiv I_s(Z) - I_s(o) \tag{11}$$
$$= I_s(o)[e^{g(\omega_s)Z} - 1].$$

The total energy in the amplified Stokes wave is $$E_s = \Delta I_s A_s T = \Delta n_s (hc\omega_s) \tag{12}$$

where $A_s$ = the cross-sectional area of the amplified Stokes beam

T = the interaction time of the pump and Stokes beams $\Delta n_s$ = the number of Stokes photons produced by the amplification process and $hc\omega_s$ = the energy of a single Stokes photon at frequency $\omega_s$.

Since, for each Stokes photon which is generated by the amplification process, one molecule is deposited in level 1, we have $\Delta n_s = \Delta n_1$ where $\Delta n_1$ is equal to the increase in the number of molecules in level 1 produced by the Stokes amplification process. Therefore $\Delta n_1$ may be written as $$\Delta n_1 = \Delta I_s A_s T / hc\omega_s. \tag{13}$$

For low-to-moderate pump intensities ($I_p$), the exponential gain factor $g(\omega_s)$ in equation (11) will be small and we can use the approximation $e^X \approx 1 + X$ for $X \ll 1$. Therefore, equation (11) may be written as $$\Delta I_s \approx g(\omega_s) Z I_s(o). \tag{14}$$

Combining equations (13) and (14) and expressing the Stokes laser intensity in units of W/cm², we obtain $$\Delta n_1 = 5.03 \times 10^{22} A_s g(\omega_s) Z I_s(o) T / \omega_s. \tag{15}$$

Equation (15) permits us to calculate directly the increase in the number of molecules in level 1 induced by the interaction of the $\omega_p$ and $\omega_s$ laser beams. The quantity, $\Delta n_1$, is directly proportional to $g(\omega_s)$ which, in turn [equation 9], is proportional to only the imaginary part of the third order nonlinear susceptibility. Because of this, there is no contribution by the real nonresonant susceptibility to the PARS signal. As a result, the PARS technique should be useful for trace analyses in mixtures.

The excess number of molecules in level 1, $\Delta n_1$, collide with other molecules in the gas and with the cell walls and, in this process, their energy ($hc\omega_V$) is converted into translational energy and these molecules return to level 0. As a result of these collisions, the internal energy, U, of the gas is increased by an amount $\Delta U$ viz., $$\Delta U = \Delta n_1 hc\omega_V \tag{16}$$

where $hc\omega_V$ is the energy of one vibrational quantum associated with level 1. Using the gas law $PV = (\gamma - 1)U$ where $\gamma$ is the ratio of the specific heat at constant pressure to that at constant volume; the pressure change produced by the change in internal energy is $$\Delta P = (\gamma - 1)\Delta U / V \tag{17a}$$

or $$\Delta P = [(\gamma - 1)\Delta n_1 hc\omega_V] / V \tag{17b}$$

where the pressure change, $\Delta P$, is in units of dynes/cm² when $\Delta U$ and V are expressed in units of ergs and cm³, respectively.

The acoustic energy, $E_A$, generated by the pressure change $\Delta P$ is equal to $V\Delta P$. Combining equations (17b) and (13) yields $$E_A = (\gamma - 1)(\omega_V / \omega_s) \Delta I_s A_s T. \tag{18}$$

The acoustic power, $P_A$, is equal to $E_A/T$, i.e., $$P_A = (\gamma - 1)(\omega_V / \omega_s) \Delta I_s A_s. \tag{19}$$

If the $\omega_p$ and $\omega_s$ laser beams have the same beam parameters (diameter and divergence angles) such that they can be exactly superimposed, then the acoustic power, $P_A$, may be written as $$P_A = (\gamma - 1)(\omega_V / \omega_s) \Delta P_s \tag{20}$$

where $$\Delta P_s = P_s(o)[e^{g(\omega_s)Z} - 1] \tag{21}$$

and $P_s(o)$ is the total incident Stokes power. From equation (14), $$\Delta P_s \approx g(\omega_s) Z P_s(o) \tag{22}$$

for low-to-moderate pump intensities.

Figure 4:
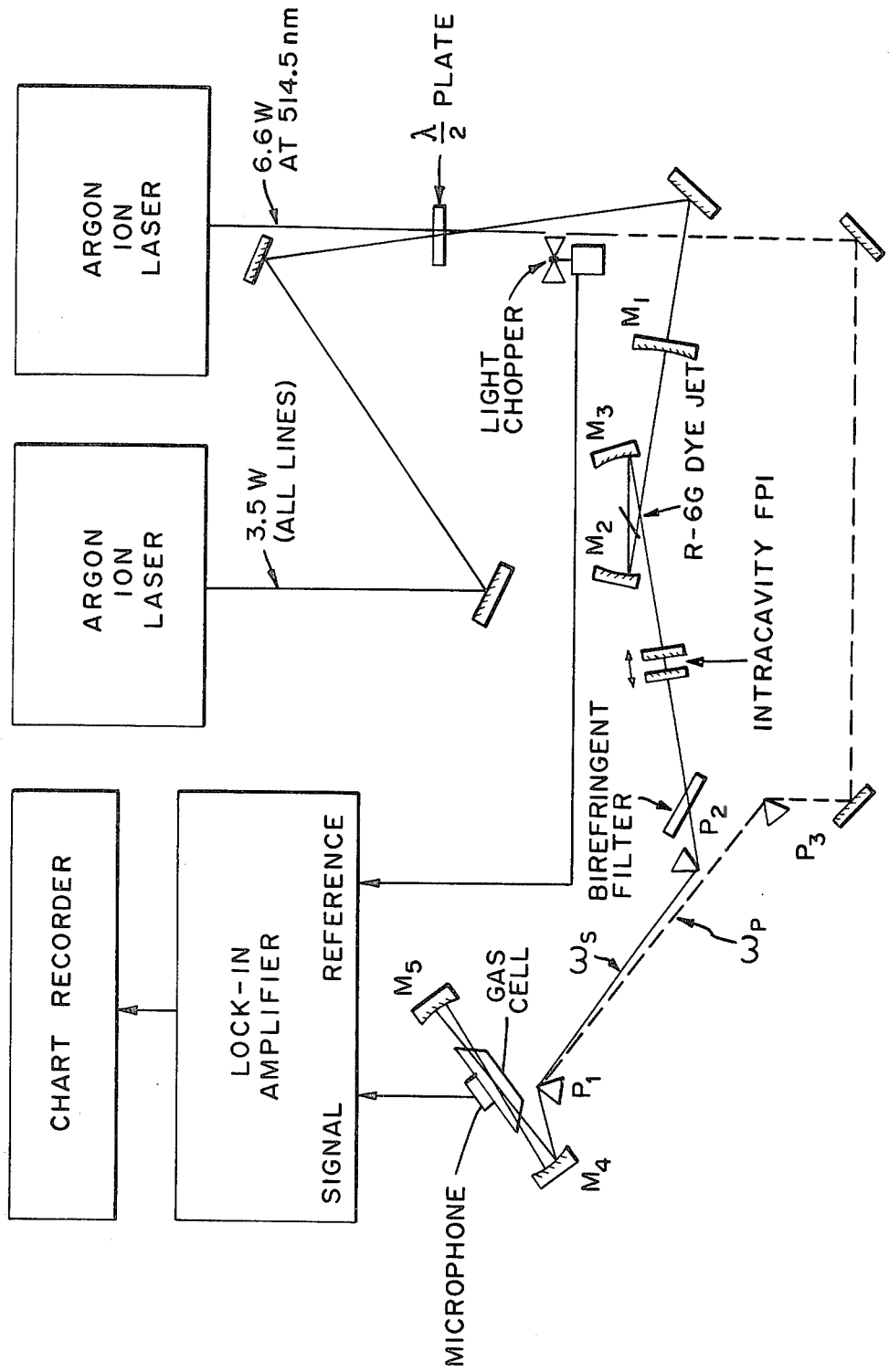
FIG. 4 is a schematic diagram of an alternative embodiment of apparatus for spectroscopic gas analysis.

Photoacoustic Raman scattering (PARS) experiments were carried out using both low power continuous wave (CW) lasers and high power pulsed lasers. A schematic representation of the experimental arrangement for the low power CW laser case is shown in FIG. 4. The 514.4 nm line of a CW argon ion laser provided the $\omega_p$ pump beam. The power in this beam was measured to be 6.6W. A second CW argon ion laser was used to pump a rhodamine-6G jet stream dye laser. This dye laser was the source of the tunable $\omega_s$ Stokes beam. The photoacoustic gas sample cell was located in the dye laser optical cavity at a focus. Mirrors and prisms were used to introduce and focus the $\omega_p$ beam into the photoacoustic cell. Care was taken to insure that the focal regions of the $\omega_p$ and $\omega_s$ beams were spatially overlapped. A birefringent filter and an intracavity Fabry-Perot interferometer were used to tune the wavelength of the dye laser. A mechanical light chopper was used to modulate the intensity of the $\omega_p$ beam and a lock-in amplifier, tuned to the chopping frequency, was employed to detect and amplify the signal from four commercial electret microphones attached to the photoacoustic cells. The output of the lock-in amplifier was displayed on a strip chart recorder.

Figure 5:
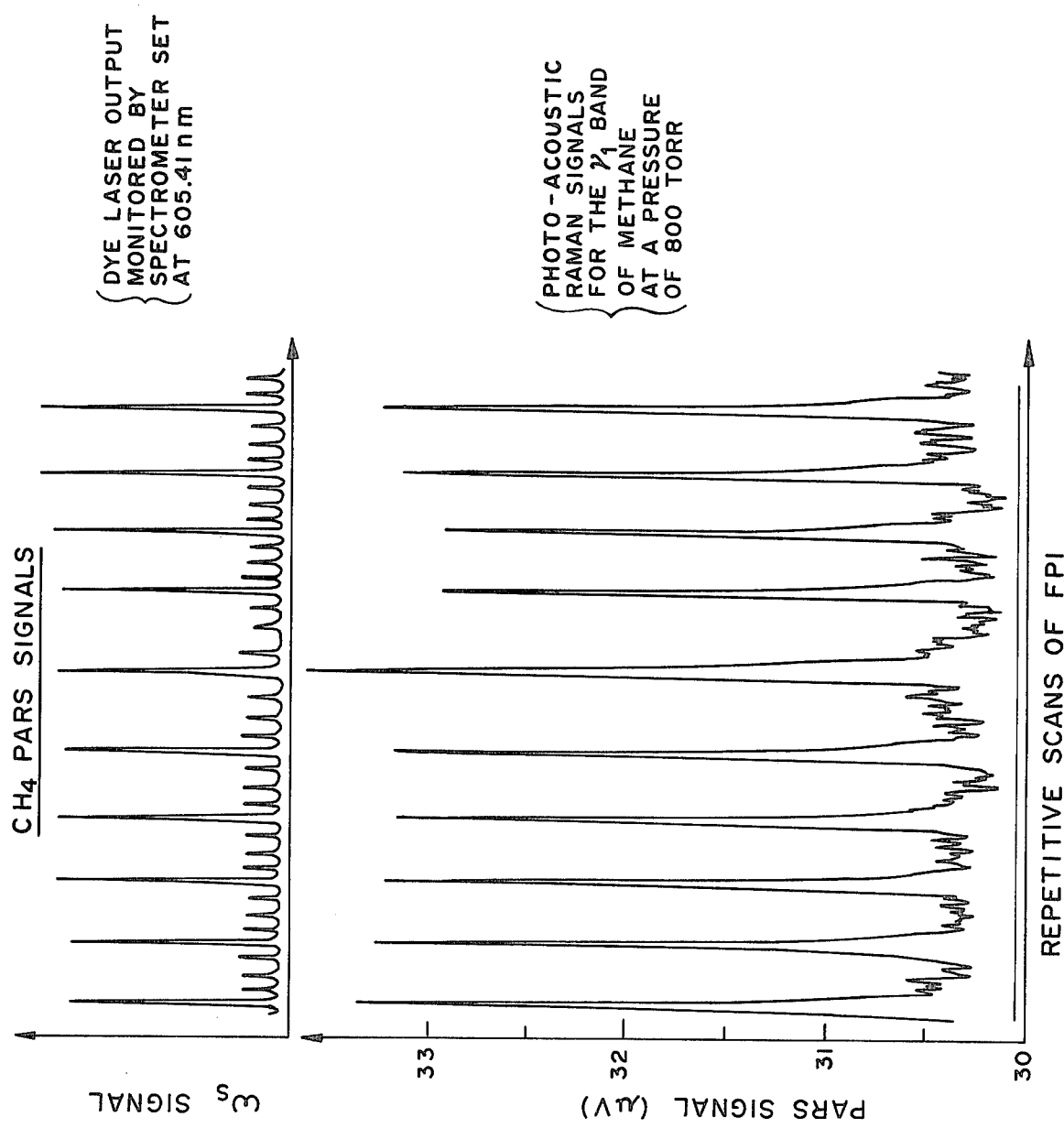
FIG. 5 is a chart showing photoacoustic signals generated in methane gas using continuous wave radiation.

With this experimental arrangement, photoacoustic Raman scattering in methane gas was investigated. The vacuum wavenumber of the 514.5 nm $\omega_p$ beam is 19429.8 cm$^{-1}$. The Raman frequency shift for the $\nu_1$ band of CH$_4$ is 2916.7 cm$^{-1}$. The Stokes vacuum wavenumber $\omega_s$ is 16513.1 cm$^{-1}$, corresponding to an air wavelength of 605.4 nm. When the dye laser was tuned to 605.4 nm an acoustic signal was generated in the cell which was detected by the microphones. The experimental results for CH$_4$ at a pressure of 800 torr are shown in FIG. 5. The upper part of the figure shows the dye laser output which was monitored by a spectrometer adjusted to transmit the Stokes wavelength. The three smaller lines between adjacent larger lines are wavelength markers which were generated by passing the $\omega_s$ radiation through a solid etalon. In the lower part of FIG. 5, the photoacoustic Raman scattering (PARS) signal for CH$_4$ is shown. The dye laser was tuned across the 605.4 nm line by piezoelectric scanning of the intracavity Fabry-Perot interferometer and repetitive scans of the $\nu_1$ band are shown in FIG. 5. The PARS signal disappeared when either the $\omega_p$ or $\omega_s$ beam was blocked. The background on the PARS signal is produced by the $\omega_p$ beam hitting a baffle in the cell. Better alignment of the photoacoustic cell reduced this background by an order of magnitude. In this experiment the magnitude of the observed PARS signals were linearly dependent upon the powers in the pump $P(\omega_p)$ and Stokes $P(\omega_s)$ beams as expected from equations (20) and (22). Also data obtained at different pressures indicate that the magnitude of the observed PARS signals are linear in molecular number density.

A numerical calculation of the PARS signal was made for conditions similar to those of the experiment. For the $\nu_1$ band of methane, the Raman scattering cross-section is $2.6 \times 10^{-30}$ cm$^2$/molecule/steradian and the Raman linewidth (FWHM) is equal to 0.9 cm$^{-1}$. The laser power in the pump beam at 514.5 nm was 10.4W for two passes through the cell and the estimated intracavity power in the Stokes beam was one watt. These laser beams were focused in the center of the photoacoustic cell with a focusing angle $\alpha$ of about 0.02 radians. The photoacoustic signal was generated mainly in the focal region where the laser intensities are the greatest. If we assume that the cross-sections of the laser beams have Gaussian profiles, then the cross-sectional area of the beams at the focus is equal to $(2\lambda^2)/(\pi\alpha^2)$ and the length of the focal region (confocal parameter) is $(8\lambda)/(\pi\alpha^2)$, which is the interaction length for the PARS process. Under these conditions, the laser intensities for the pump and Stokes beams at the focus are 2.5 MW/cm$^2$ and 0.17 MW/cm$^2$, respectively and the interaction length is 0.33 cm. Using equation (10), we calculate the Stokes gain coefficient for 800 torr of CH$_4$ to be $1.5 \times 10^{-5}$ per cm. The pump laser was chopped at a frequency of 573 Hz and, therefore, the interaction time for one chopper cycle was $8.7 \times 10^{-4}$ sec. The amplified Stokes intensity [equation (11)] is $8.4 \times 10^6$ ergs/sec/cm$^2$. Therefore, using equation (13), the increase in population of the $\nu_1$ vibrational level of CH$_4$ during one chopper cycle is $1.3 \times 10^{10}$ molecules. For a cell volume of 0.5 cm$^3$ and a ratio of specific heats of 1.31 for CH$_4$, the pressure change as determined from equation (17b) is $4.7 \times 10^{-3}$ $\mu$ bars. The sensitivity of each of the four electret microphones attached to the photoacoustic cell is about 1mV/$\mu$ bar. The magnitude of the observed photoacoustic signal was 4.4$\mu$V. A pressure change of $4.7 \times 10^{-3}$ $\mu$ bars should produce a signal of 19$\mu$V which differs from the observed signal by a factor of four. This agreement between theory and experiment is quite good considering the uncertainties involved in estimating the laser beam parameters.

Experiments have also been conducted on the generation of PARS signals by means of high power pulsed lasers. The experimental arrangement for these experiments is shown schematically in FIG. 2. It is advantageous to use high power pulsed lasers to generate PARS signals since the efficiency of the PARS technique increases with increasing intensities of the pump and Stokes beams. Experimental results for CO$_2$ gas are shown in FIG. 6.

Having thus described the invention in rather full detail, it will be understood that these details need not be strictly adhered to but that various changes and modifications may suggest themselves to one skilled in the art, all falling within the scope of the present invention as defined by the subjoined claims.

We claim:

1. Apparatus for analyzing material, comprising:
   a. radiation source means (12) for generating two coherent beams (15, 17) of monochromatic light;
   b. tuning means (14) for adjusting the frequency difference between said beams (15, 17) of radiation to equal substantially the vibrational frequency of a preselected constituent of said material;
   c. projecting means (16) for directing said beams of light through said material to increase molecular energy of a preselected species of said material and thereby produce a detectable signal (22) in the form of a pressure wave;
   d. detecting means (24) for indicating the magnitude of said signal.

2. Apparatus as recited in claim 1, wherein said tuning means (14) is adjusted to selectively populate a higher energy level of said preselected molecular species.

3. Apparatus as recited in claim 1, wherein said projecting means (16) is adjusted to effect spatial and temporal overlap between said radiation beams (15, 17).

4. Apparatus as recited in claim 1, wherein said radiation source means (12) comprises a dye laser (24) including a dye cell (28) containing a dye material, means for exciting said dye (26) and a laser cavity comprised of an optical element (32) and a partially transmitting output mirror (30) for generating and transmitting laser radiation.

5. Apparatus as recited in claim 4, wherein said dye material emits radiation upon being excited, said radiation having frequencies within the transparency range of said material.

6. Apparatus as recited in claim 1, wherein said tuning means comprises beam splitting means for separating said radiation into a pair of radiation beams, and a pair of diffraction gratings mounted in autocollimation.

7. A method for spectroscopically analyzing material comprising the steps of:
   a. generating two coherent beams (15, 17) of monochromatic radiation;
   b. adjusting the frequency difference between the beams of radiation (15, 17) to equal substantially the vibrational frequency of a preselected constituent of said material;
   c. directing the beams of radiation through the material to produce a detectable signal (22) in the form of a pressure wave; and
   d. indicating the intensity of said signal (22).

* * * * *